United States Patent [19]

Hagiwara et al.

[11] Patent Number: 5,220,923
[45] Date of Patent: Jun. 22, 1993

[54] ULTRASONIC DOPPLER BLOOD FLOWMETER

[75] Inventors: Hisashi Hagiwara, Yokohama; Hiroshi Fukukita, Tokyo; Yoshinobu Watanabe, Yokohama; Yoshinao Tannaka, Kawasaki, all of Japan

[73] Assignee: Matsushita Electric Industrial Co., Ltd., Kadoma, Japan

[21] Appl. No.: 746,416

[22] Filed: Aug. 16, 1991

[30] Foreign Application Priority Data

Aug. 20, 1990 [JP] Japan .................................. 2-219234
Aug. 20, 1990 [JP] Japan .................................. 2-219235

[51] Int. Cl.$^5$ ................................................ A61B 8/06
[52] U.S. Cl. ............................ 128/661.09; 73/861.25
[58] Field of Search ...................... 128/661.08–661.10; 73/861.25

[56] References Cited

U.S. PATENT DOCUMENTS

| 4,265,126 | 5/1981 | Papadofrangakis et al. .... 73/861.25 |
| 4,800,891 | 1/1989 | Kim ................................. 128/661.09 |
| 4,817,617 | 4/1989 | Takeuchi et al. ........... 128/661.09 X |
| 4,848,354 | 7/1989 | Angelsen et al. ........... 128/661.09 X |
| 4,905,206 | 2/1990 | Nishiyama et al. ............ 128/661.09 |
| 4,930,514 | 6/1990 | Baba et al. ...................... 128/661.09 |

FOREIGN PATENT DOCUMENTS

| 0254400 | 1/1988 | European Pat. Off. . |
| 0399734 | 11/1990 | European Pat. Off. . |
| 55-54941 | 4/1955 | Japan . |
| 61-25534 | 2/1961 | Japan . |

OTHER PUBLICATIONS

"A Time-Shared Ultrasound Doppler Measurement and 2D Imaging System" Kristofferson et al., IEEE Transactions on Biomedical Engineering vol. 35, No. 5, May 1988, pp. 285–297.

*Primary Examiner*—Francis Jaworski
*Attorney, Agent, or Firm*—Spencer, Frank & Schneider

[57] ABSTRACT

An ultrasonic Doppler blood flowmeter has a Doppler scanning mode of operation to obtain information about blood speed and a B mode of operation to obtain information for a tomogram. In order to produce supplementary Doppler shift data for use during a B-mode scanning period, Doppler shift data from a phase detector is treated as complex data, and the difference in argument between two consecutive, complex Doppler shift data is detected. The supplementary Doppler shift data can then be calculated by an arithmetic circuit on the basis of the difference in argument between the consecutive complex Doppler shift data.

4 Claims, 12 Drawing Sheets

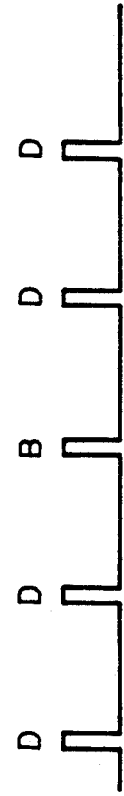
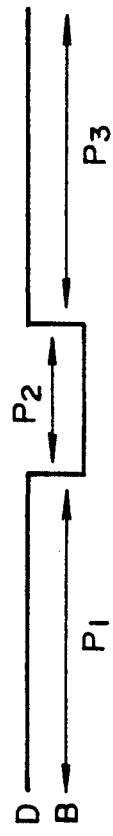
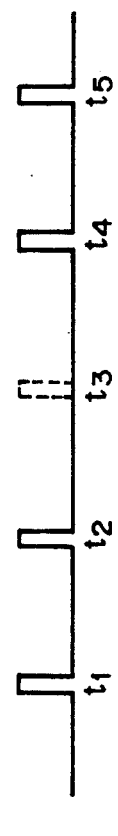
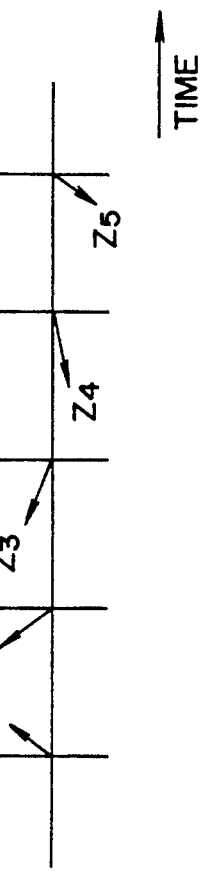
FIG. 4A TRANSMITTED PULSE
FIG. 4B SWITCH
FIG. 4C OUTPUT OF DETECTION CIRCUIT
FIG. 4D DOPPLER GATE SIGNAL
FIG. 4E OUTPUTS OF SAMPLE HOLD CIRCUITS
FIG. 4F OUTPUTS OF INTER- POLATION CIRCUIT

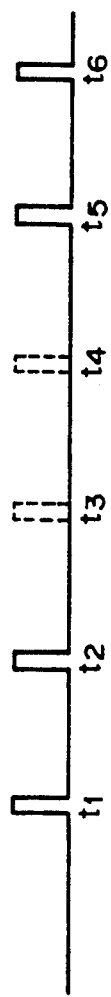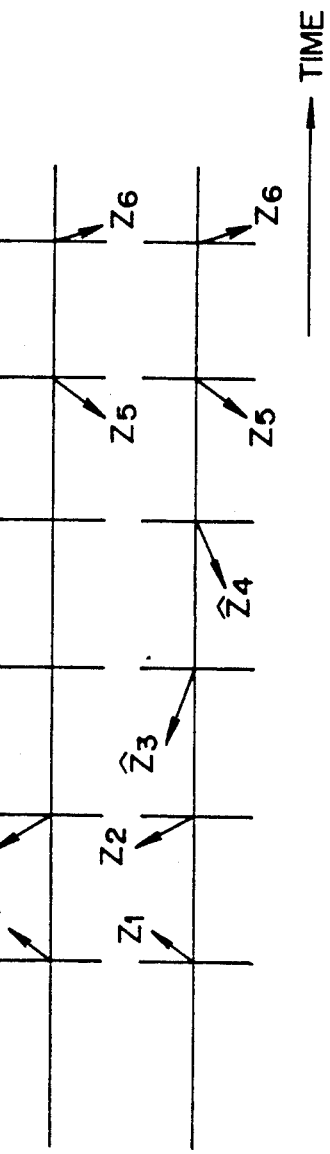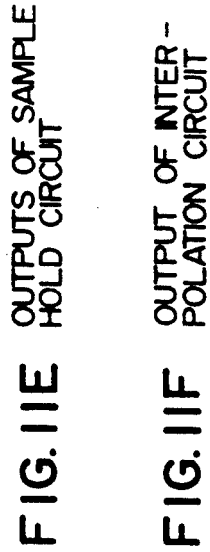
FIG. 11A TRANSMITTED PULSE
FIG. 11B SWITCH
FIG. 11C OUTPUT SIGNAL OF DETECTION CIRCUIT
FIG. 11D DOPPLER GATE SIGNAL
FIG. 11E OUTPUTS OF SAMPLE HOLD CIRCUIT
FIG. 11F OUTPUT OF INTER- POLATION CIRCUIT

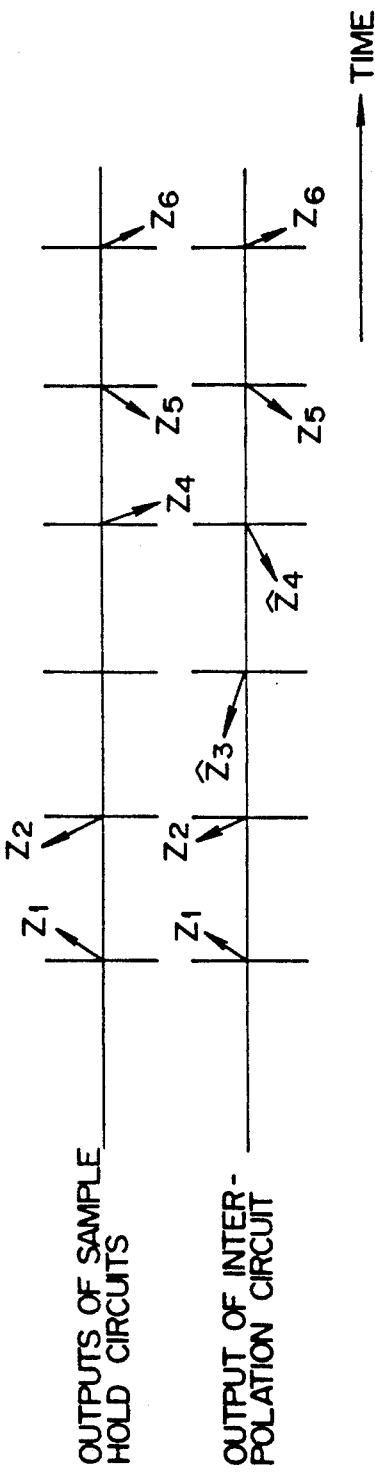
FIG. 12A TRANSMITTED PULSE
FIG. 12B SWITCH
FIG. 12C OUTPUT SIGNAL OF DETECTION CIRCUIT
FIG. 12D DOPPLER GATE SIGNAL
FIG. 12E OUTPUTS OF SAMPLE HOLD CIRCUITS
FIG. 12F OUTPUT OF INTERPOLATION CIRCUIT

5,220,923

ULTRASONIC DOPPLER BLOOD FLOWMETER

BACKGROUND OF THE INVENTION

The present invention relates to an ultrasonic Doppler blood flowmeter which can carry out imaging using ultrasonic waves, and which can simultaneously measure the speed of a moving fluid based upon the pulse Doppler method.

In recent years, an ultrasonic Doppler blood flowmeter has been employed which can display a sonagram based upon the Doppler effect and a tomogram due to ultrasonic waves at the same time and in real time by using both of the ultrasonic pulse Doppler method and the ultrasonic pulse reflection method. This ultrasonic Doppler blood flowmeter has been widely used for diagnosing the cardiovascular system and organs of a living body. The construction of the above ultrasonic Doppler blood flowmeter is described in, for example, Japanese patent application JP-A-sho 55-54,941. This conventional ultrasonic Doppler blood flowmeter will be explained below, with reference to FIG. 1.

FIG. 1 is a block diagram for explaining the basic principle of the conventional ultrasonic Doppler blood flowmeter. In FIG. 1, reference numeral 90 designates a probe, 91 designates a transmitting/scanning circuit, 92 designates a receiving/scanning circuit, 93 designates a phase detector, 94 designates a frequency analyzer, 95 designates an amplitude detector, 96 designates a display device, and 97 designates a controller.

Next, the operation of the above blood flowmeter will be explained. A drive pulse, which is generated by the transmitting/scanning circuit 91, is applied to the probe 90, to transmit an ultrasonic wave in directions $m_1, m_2, \ldots$ and $m_n$. The receiving/scanning circuit 92 is controlled so as to have high sensitivity in the directions $m_1, m_2, \ldots$ and $m_n$. In the Doppler mode, ultrasonic waves are repeatedly transmitted and received in a specified direction, for example, in a direction $m_d$. The received signal is subjected to phase detection, to obtain I- and Q-signals which indicate Doppler shift data. The I- and Q-signals are subjected to frequency analysis, to determine the moving speed of blood in a body that is being inspected, and the speed is displayed on the display screen of the display device 96. In the B-mode, the transmission and reception of ultrasonic waves are carried out successively in the directions $m_1, m_2$ and so. The received signal thus obtained is subjected to envelope detection by the amplitude detector 95, to display a tomogram on the display screen of the display device 96. Either the Doppler mode or the B-mode is selected by the controller 97. In order to obtain information on the flow of blood in a sampling volume S existing in the direction $m_d$ and a tomogram due to the B-mode at the same time, the transmission and reception of ultrasonic waves in the directions $m_1, m_2, \ldots$ and $m_n$ due to the B-mode and the transmission and reception of ultrasonic waves in the direction $m_d$ due to the Doppler mode are alternately carried out on the basis of a command from the controller 97. This operation mode will hereinafter be referred to as "B/D mode".

When the repetition frequency of ultrasonic pulses in the Doppler mode is expressed by fr, the repetition frequency of Doppler operation in the B/D mode may be reduced to fr/2. Thus, there arises the problem that the maximum measurable blood speed is reduced to the half of the maximum measurable blood speed in the Doppler mode.

In order to solve this problem, a method has been devised which can obtain a tomogram due to the B-mode, without reducing the sampling frequency of Doppler data. An example of this method is described in Japanese patent application JP-A-sho 61-25,534. According to this method, the transmission and reception of ultrasonic waves in the Doppler mode are repeated three times and then the transmission and reception of ultrasonic waves in the B-mode are once carried out by using, for example, the blood flowmeter of FIG. 1. The output of the phase detector 93, which is not generated during the period when the flowmeter is operated in the B-mode, is calculated by an interpolation method. Thus, the sampling frequency of Doppler shift data is not reduced.

The interpolation method in this case, however, has been devised to process a conversational or voice signal, and is not suited to produce supplementary data for a signal having a frequency component corresponding to half of the sampling frequency, such as Doppler shift data according to the above operation. FIG. 2 shows the results of the above interpolation method for Doppler shift data which is obtained by transmitting ultrasonic pulses twice in the Doppler mode and by transmitting an ultrasonic pulse once in the B-mode, and thus has a frequency component corresponding to half of the repetition frequency of the transmitted pulses. As shown in FIG. 2, a supplementary value obtained by the interpolation method is entirely different from the expected value. In other words, a frequency which is obtained on the basis of the supplementary value is shifted to the low frequency side. Thus, there arises the problem that the frequency obtained by the frequency analyzer is different from the correct frequency.

SUMMARY OF THE INVENTION

It is an object of the present invention to provide an ultrasonic Doppler blood flowmeter which can solve the problems of prior art, and which can produce a correct, supplementary value of the Doppler shift data even if the Doppler shift data has a frequency component corresponding to half of the repetition frequency of transmitted pulses in the Doppler mode, by an interpolation method.

In order to attain the above object, according to a first aspect of the present invention, there is provided an ultrasonic Doppler blood flowmeter which includes data interpolation means for regarding Doppler shift data from a phase detector as complex data, to determine the difference in argument between adjacent complex Doppler shift data and to produce supplementary data on the basis of the difference in argument.

According to a second aspect of the present invention, there is provided an ultrasonic Doppler blood flowmeter which includes data interpolation means for producing supplementary data by an extrapolation method on the basis of the difference in argument between adjacent complex Doppler shift data.

According to a third aspect of the present invention, there is provided an ultrasonic Doppler blood flowmeter which includes control means for stopping the transmission and reception of an ultrasonic wave in the Doppler mode for a predetermined period, after the transmission and reception of the ultrasonic wave in the Doppler mode for obtaining a Doppler shift signal have been carried out at least twice, Doppler signal detection means for detecting the Doppler shift signal, argument interpolation means for calculating the argument of a missing, complex Doppler shift signal in the period when the transmission and reception of the ultrasonic wave in the Doppler mode are stopped, from Doppler shift signals obtained before and after the period, by an interpolation method, and amplitude interpolation means for calculating the amplitude of a missing, complex Doppler shift signal in the period when the transmission and reception of the ultrasonic wave in the Doppler mode are stopped, from Doppler shift signal obtained before and after the period, by the interpolation method.

According to a fourth aspect of the present invention, there is provided an ultrasonic Doppler blood flowmeter which includes data interpolation means for calculating Doppler shift signals in a period when the transmission and reception of an ultrasonic wave in the Doppler mode are stopped and which is at least twice longer than a sampling period for obtaining Doppler shift signals, from Doppler shift signal obtained before and after the period, by an interpolation method.

An ultrasonic Doppler blood flowmeter according to the first aspect of the present invention has an advantage in that, in the B/D mode, supplementary data can be correctly produced for Doppler shift data having a frequency component corresponding to the half of a sampling frequency in the Doppler mode.

Further, an ultrasonic Doppler blood flowmeter according to the second aspect of the present invention has an advantage in that, in the B/D mode, supplementary data can be correctly produced by the extrapolation method.

Furthermore, an ultrasonic Doppler blood flowmeter according to the third aspect of the present invention has the following advantage. That is, in a case where the transmission and reception of a Doppler pulse are carried out at least twice in a consecutive manner and then stopped for a period longer than one sampling period in the Doppler mode, missing Doppler data in the period when the transmission and reception of a Doppler pulse are stopped, can be correctly calculated from the argument and absolute value of each of actual Doppler data obtained before and after the above period, and thus a train of Doppler data substantially equal to that obtained by sampling a Doppler signal at regular intervals can be formed.

Additionally, an ultrasonic Doppler blood flowmeter according to the fourth aspect of the present invention has an advantage in that even in a case where the transmission and reception of a Doppler pulse are stopped for a period which is at least twice as long as the sampling period in the Doppler mode, missing Doppler data in the above period can be correctly produced by the interpolation method.

BRIEF DESCRIPTION OF THE DRAWINGS

FIGS. 4A, 4B, 4C, 4D, 4E and 4F are timing charts for explaining a first example of the operation of the embodiment of FIG. 3.

FIGS. 11A, 11B, 11C, 11D, 11E and 11F are timing charts for explaining a third example of the operation of the embodiment of FIG. 3.

FIGS. 12A, 12B, 12D, 12E and 12F are timing charts for explaining a fourth example of the operation of the embodiment of FIG. 3.

DESCRIPTION OF THE PREFERRED EMBODIMENT

Figure 3:
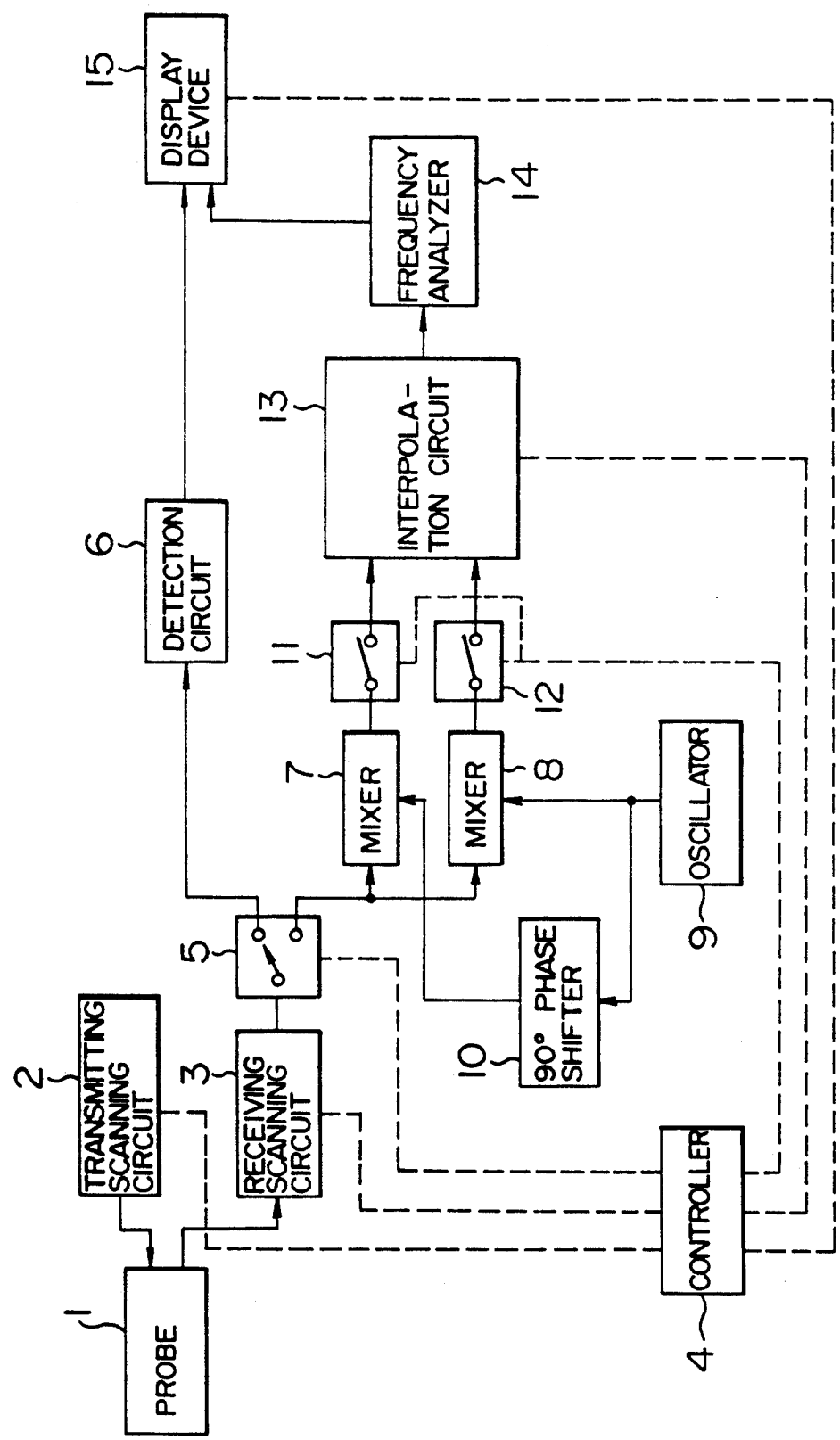
FIG. 3 is a block diagram showing an embodiment of an ultrasonic Doppler blood flowmeter according to the present invention.

An embodiment of an ultrasonic Doppler blood flowmeter according to the present invention will be explained below, with reference to the drawings. FIG. 3 shows an embodiment of an ultrasonic Doppler blood flowmeter according to the present invention. In FIG. 3, solid lines indicate signal paths, and broken lines indicate control paths. Further, in FIG. 3, reference numeral 1 designates a probe, 2 designates a transmitting/scanning circuit, 3 designates a receiving/scanning circuit, 4 designates a controller, 5 designates a switch, 6 designates a detection circuit, 7 and 8 designate mixers, 9 designates an oscillator, 10 designates a phase shifter, 11 and 12 designate sample/hold circuits, 13 designates an interpolation circuit, 14 designates a frequency analyzer, and 15 designates a display device. The operation of the present embodiment having the above construction will be explained below. When a drive pulse is supplied from the transmitting/scanning circuit 2 to the probe 1, the probe 1 transmits an ultrasonic pulse to an object to be inspected. The ultrasonic pulse is scattered by the to-be-inspected object, and the probe 1 converts it into an electric signal which is sent to the receiving/scanning circuit 3. Each of the transmitting/scanning circuit 2 and the receiving/scanning circuit 3 carries out B-mode scanning and Doppler scanning time-divisionally in accordance with a command from the controller 4. The switch 5 is controlled by a command from the controller 4 so that an ultrasonic echo signal from the receiving/scanning circuit 3 is sent to the detection circuit 6 during the period when the B-mode scanning is carried out, and to the mixers 7 and 8 during the period when the Doppler scanning is carried out. The ultrasonic echo signal from the switch 5 and the output signal of the oscillator 9 are mixed by the mixer 8, and the ultrasonic echo signal from the switch 5 and the output signal of the 90° phase shifter 10 (that is, a signal 90° out of phase with the output signal of the oscillator 9) are mixed by the mixer 7, to detect a Doppler signal. The sample/hold circuits 11 and 12 are supplied with a gate signal from the controller 4 and corresponding to a part which is to be inspected in the Doppler mode, to perform sampling operations for the Doppler signal > from the mixers 7 and 8. ,In the interpolation circuit 13, missing Doppler data, during the period when the transmission and reception of ultrasonic waves in the Doppler mode are stopped in accordance with a command from the controller 4, is calculated on the basis of the Doppler signal from the sample/hold circuits 11 and 12 by an interpolation method. The missing Doppler data thus obtained is added to Doppler data obtained during the period when the transmission and reception of ultrasonic waves in the Doppler mode are carried out. Thus, a train of Doppler data arranged in regular order is obtained, and sent to the frequency analyzer 14. In the frequency analyzer 14, Fourier analysis or the like is carried out. The result of this analysis is sent, as a Doppler image signal, to the display device 15. In the display device 15, the B-mode image signal from the detection circuit 6 and the Doppler image signal from the frequency analyzer 14 are simultaneously displayed under the control of the controller 4.

Figure 1:
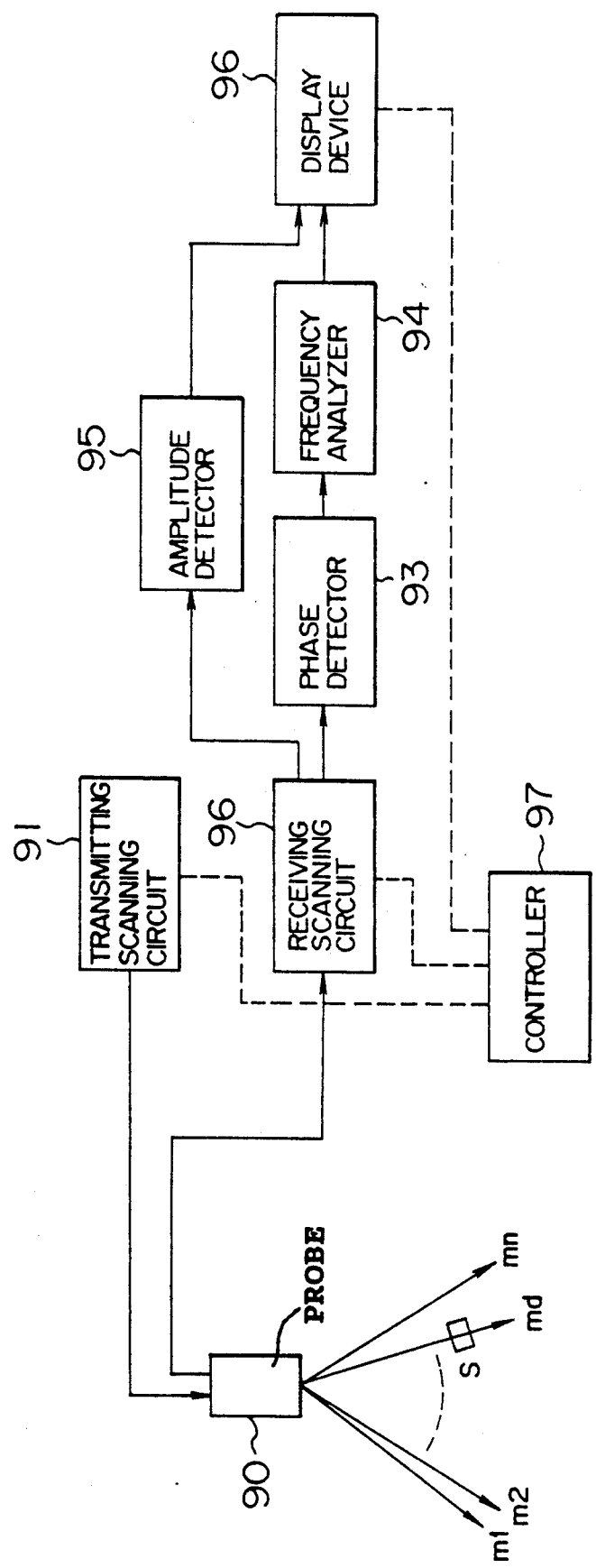
FIG. 1 is a diagram showing a conventional ultrasonic Doppler blood flowmeter.
Figure 2:
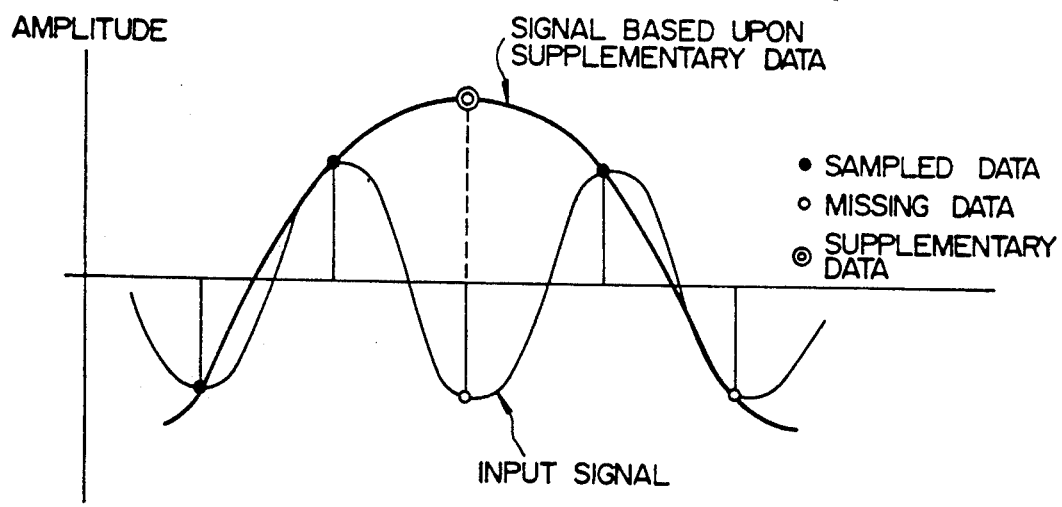
FIG. 2 is a waveform chart for explaining an interpolation method used in the conventional blood flowmeter of FIG. 1.

An example of the operation of the present embodiment will now be presented with reference to FIGS. 4A to 4F. In this example, Doppler scanning is carried out twice, B-mode scanning is then carried out once, and this combination of scanning is carried out repeatedly FIG. 4A shows transmitted pulses from the transmitting/scanning circuit 2. FIG. 4B shows the connecting state of the switch 5. In FIG. 4B, the level D indicates that the input of the switch 5 is applied to the mixers 7 and 8, and a level B indicates that the input of the switch 5 is applied to the detection circuit 6. FIG. 4C shows the output signal of the detection circuit 6. FIG. 4D shows the Doppler gate signal supplied from the controller 4 for controlling the sample/hold circuits 11 and 12. FIG. 2E shows vectors, the real and imaginary parts of which are given by the outputs of the sample/hold circuits 11 and 12, respectively. FIG. 4F shows the output of the interpolation circuit 13 expressed by a vector.

The transmitting/scanning circuit 2 sends Doppler scanning pulses D and the B-mode scanning pulse B to the probe 1, as shown in FIG. 4A. As shown in FIG. 4B, the switch 5 sends the output of the receiving/scanning circuit 3 to the mixers 7 and 8 in each of periods $P_1$ and $P_3$ (namely, in the Doppler scanning periods), and sends the output of the receiving/scanning circuit 3 to the detection circuit 6 in a period $P_2$ (namely, in a period when the Doppler scanning is stopped). In the period $P_2$, information on one scanning line for forming a tomogram due to the B-mode operation is obtained, and the detection circuit 6 carries out enveloped detection for the information, as shown in FIG. 4C. In the Doppler scanning periods $P_1$ and $P_3$, the sample/hold circuits 11 and 12 perform sampling operations for the quadrature phase detection output from the mixers 7 and 8 at times $t_1$, $t_2$, $t_4$ and $t_5$ in accordance with the Doppler gate signal of FIG. 4D, as shown in FIG. 4E. In the interpolation circuit 13, as shown in FIG. 4F, a Doppler signal $Z_3$, which would be obtained at a time $t_3$ if the B-mode scanning period $P_2$ were a Doppler scanning period, is calculated from the Doppler data at the times $t_1$ and $t_2$.

Figure 5:
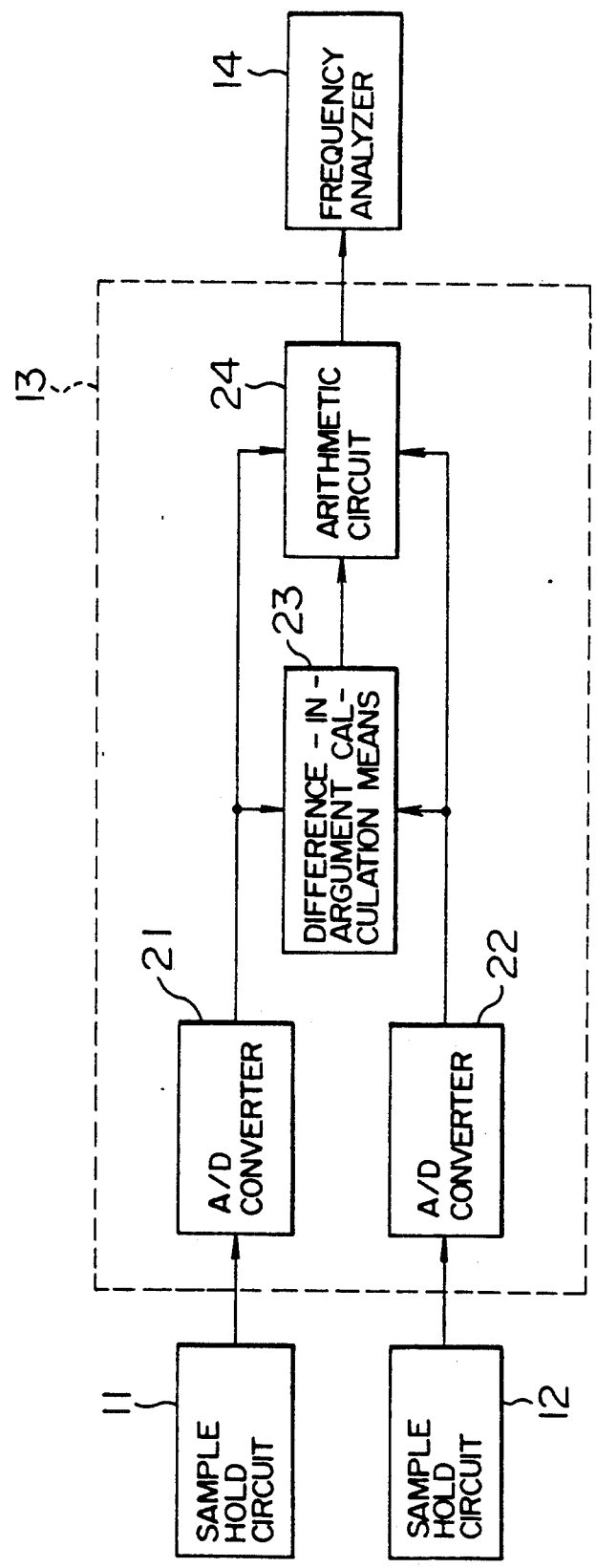
FIG. 5 is a block diagram showing a first example of the interpolation circuit of FIG. 3.

FIG. 5 is a block diagram showing an example of the interpolation circuit 13. In FIG. 5, reference numerals 21 and 22 designate A-D converters, 23 designates difference-in-argument calculation means, and 24 designates an arithmetic circuit for generating supplementary data. The outputs of the sample/hold circuits 11 and 12 are converted into digital signals by the A-D converters 21 and 22, respectively. The outputs of the sample/hold circuits 11 and 12 can be treated as a complex number. Accordingly, the outputs of the A-D converters 12 and 22 will hereinafter be referred to as "complex Doppler shift data". In the difference-in-argument calculation means 23, the difference $\Delta\theta$ in argument between the complex Doppler shift data $Z_1$ at the sampling time $t_1$ and the complex Doppler shift data $Z_2$ at the sampling time $t_2$ is calculated. The arithmetic circuit 24 calculates supplementary data $Z_3$ on the basis of the above difference $\Delta\theta$ and the complex Doppler shift data, and delivers the measured Doppler shift data $Z_1$ and $Z_2$ and the calculated data $Z_3$ in regular order. As can be seen from the above, the supplementary data $Z_3$ is obtained by the extrapolation method.

An example of the calculation of supplementary data will be explained below. The complex Doppler shift data $Z_1$ and $Z_2$ can be expressed by $(x_1+jy_1)$ and $(x_2+jy_2)$, respectively. The argument $\theta_1$ of the complex Doppler shift data $Z_1$ is given by the following equation:

$$\theta_1 = \tan^{-1}(y_1/x_1) \qquad (1)$$

Further, the argument $\theta_2$ f the complex Doppler shift data $Z_2$ is given by an equation similar to the equation (1).

The difference $\Delta\theta$ in argument between the complex data $Z_1$ and $Z_2$ is given by the following equation:

$$\Delta\theta = \theta_2 - \theta_1 \qquad (2)$$

When a Doppler signal is expressed by a complex number, it is unusual for each of the absolute value of the complex number and the difference $\Delta\theta$ in argument to vary abruptly. Accordingly, the argument $\theta$ of the supplementary data $Z_3$ is given by the following equation:

$$\theta = 2 + \Delta\theta \qquad (3)$$

When it is supposed that the absolute value of supplementary data $Z_3$ is equal to the absolute value of the complex Doppler shift data $Z_2$, the supplementary data $Z_3$ is given by the following equation:

$$Z_3 = r_2 \times (\cos\theta + j\sin\theta) \qquad (4)$$

where $r_2 = |x_2+jy_2|$

By utilizing the fact that it is unusual for each of the absolute value of complex Doppler shift data and the difference in argument between adjacent Doppler shift data to vary abruptly, supplementary data can be calculated in various ways. For example, the supplementary data $Z_3$ may be given by the equation $Z_3 = Z_2 \cdot Z_2/Z_1$.

As mentioned above, even if the Doppler shift data has a frequency component corresponding to half of the repetition frequency of the transmitted pulses in the Doppler mode, supplementary data can be correctly calculated on the basis of the absolute value of the complex Doppler shift data and the difference in argument between adjacent Doppler shift data. That is, missing Doppler shift data in a period when the transmission and reception of ultrasonic waves in the Doppler mode are stopped, can be correctly calculated.

Figure 6:
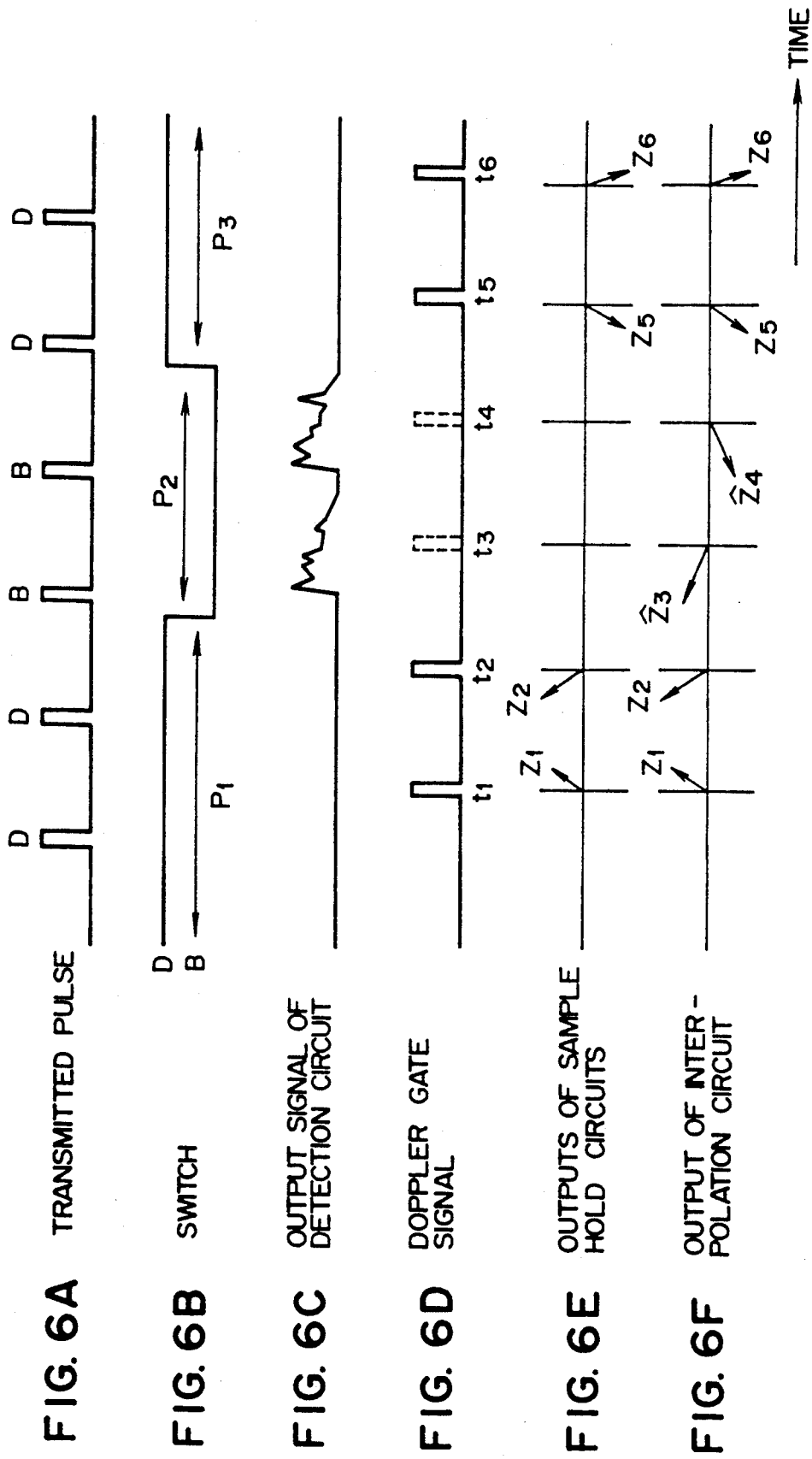
FIGS. 6A, 6B, 6C, 6D, 6E and 6F are timing charts for explaining a second example of the operation of the embodiment of FIG. 3.

Next, a second example the operation of the present embodiment will be explained with reference to FIGS. 6A to 6F. In this example, the Doppler scanning is carried out twice, the B-mode scanning is then carried out twice, and this combination of scanning is repeatedly carried out. FIG. 6A shows transmitted pulses from the transmitting/scanning circuit 2. FIG. 6B shows the connecting state of the switch 5. In FIG. 6B, the level D indicates that an input to the switch 5 is applied to the mixers 7 and 8, and the level B indicates that an input to the switch 5 is applied to the detection circuit 6. FIG. 6C shows the output signal of the detection circuit 6. FIG. 6D shows a Doppler gate signal supplied from the controller 4 for controlling the sample/hold circuits 11 and 12. FIG. 6E shows vectors, the real and imaginary parts of which are given by the outputs of the sample/hold circuits 11 and 12, respectively. FIG. 6F shows the output of the interpolation circuit 13 expressed by a vector.

The transmitting/scanning circuit 2 sends Doppler pulses D and B-mode pulses B to the probe 1, as shown in FIG. 6A. As shown in FIG. 6B, the switch 5 sends the output of the receiving/scanning circuit 3 to the mixers 7 and 8 in each of the periods $P_1$ and $P_3$ (namely, in the Doppler scanning periods), and sends the output of the receiving/scanning circuit 3 to the detection circuit 6 in the period $P_2$ (namely, in the B-mode scanning period). In the B-mode scanning period $P_2$, information on two scanning lines for forming a tomogram due to the B-mode operation is obtained, and the detection circuit 6 carries out envelope detection for the information, as shown in FIG. 6C. In the Doppler scanning periods $P_1$ and $P_3$, the sample/hold circuits 11 and 12 perform sampling operations for quadrature phase detection output from the mixers 7 and 8 at times $t_1$, $t_2$, $t_5$, and $t_6$ in accordance with the Doppler gate signal of FIG. 6D, as shown in FIG. 6E. In the interpolation circuit 13, as shown in FIG. 6F, Doppler signals $\hat{Z}_3$ and $\hat{Z}_4$ which would be obtained at time moments $t_3$ and $t_4$ if the B-mode scanning period $P_2$ were a Doppler scanning period, are calculated from Doppler data at the times $t_1$, $t_2$, $t_5$ and $t_6$.

Figure 7:
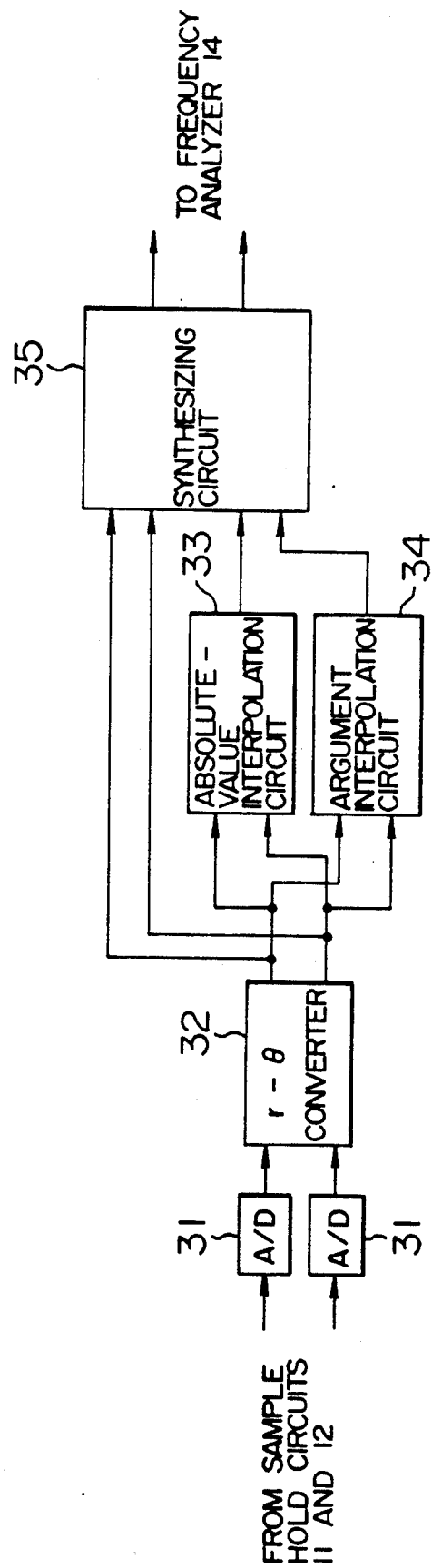
FIG. 7 is a block diagram showing a second example of the interpolation circuit of FIG. 3.

FIG. 7 shows another example of the interpolation circuit 13. Referring to FIG. 7, analog signals from the sample/hold circuits 11 and 12 are converted by A-D converters 31 into digital signals, and orthogonal data from the A-D converters 31 is converted by an r/θ converter (that is, orthogonal-polar converter) 32 into polar coordinate values. Doppler data expressed by the polar coordinate values is sent to an absolute-value interpolation circuit 33 and an argument interpolation circuit 34, to obtain the missing Doppler data in the B-mode scanning period $P_2$ by calculation. The result of the calculation is sent to a synthesizing circuit 35. The Doppler data measured directly and the supplementary data obtained by calculation are delivered from the circuit 35 in regular order.

An example of the calculation of supplementary data in a case where, as shown in FIGS. 6B and 6D, the Doppler scanning period $P_1$ and $P_3$ is twice as long as the Doppler sampling period and the B-mode scanning period $P_2$ is also twice as long as the Doppler sampling period, will be explained below.

Now, let us express the Doppler data (that is, a complex vector) which is detected at a time $t_i$ (where i=1, 2, 5, or 6) and which is delivered from the sample/hold circuits 11 and 12, by $Z_i = a_i + jb_i$. This Doppler data, which is obtained from the A-D converters 31, can then be expressed by polar coordinate values with the aid of the r/θ converter 32. That is, the Doppler data $Z_i$ is transformed to Doppler Data $Z_\lambda$ in accordance with the equation $Z_\lambda = r_i e^{j\theta_i}$ (where $r_i$ indicates the absolute value of the complex data $Z_i$, and $\theta_i$ indicates the argument thereof and satisfies the relation $-\pi < \theta \leq \pi$). Missing Doppler data $\hat{Z}_3 = r_3 e^{j\theta_3}$ and $Z_4 = r_4 e^{j\theta_4}$ at the times $t_3$ and $t_4$ can be calculated in the following manner.

In the absolute-value interpolation circuit 33, it is assumed that the absolute value of the complex Doppler data varies linearly in the period from the time $t_2$ to the time $t_5$, and thus the absolute values $r_3$ and $r_4$ are given by the following equations:

$$r_3 = (2r_2 + r_5)/3 \qquad (5)$$

$$r_4 = (r_2 + 2r_5)/3 \qquad (4)$$

In the argument interpolation circuit 34, it is assumed that the argument of the complex Doppler data varies linearly in the period from the time $t_2$ to the time $t_5$. In some cases, however, the argument of the complex Doppler data may vary by an angle greater than $\pi$ in the above period, because the period from the time $t_2$ to the time $t_5$ is three times longer than the Doppler sampling period. Accordingly, the true difference $\theta_d$ between the argument $\theta_5$ at the time $t_5$ and the argument $\theta_2$ at the time $t_2$ is given by the following equation:

$$\theta_d = (\theta_5 - \theta_2) + 2\pi n \qquad (7)$$

when n is an integer.

While, the mean value (w) of the difference between the argument $\theta_1$ at the time $t_1$ and the argument $\theta_2$ at the time $t_2$ and the difference between the argument $\theta_5$ at the time $t_5$ and the argument $\theta_6$ at the time $t_6$ can be expressed by the following equation:

$$\omega = \{(\theta_2 - \theta_1) + (\theta_6 - \theta_5)\}/2 \qquad (8)$$

Now, let us suppose that the difference between the argument at the time $t_2$ and the argument at the time $t_3$, the difference between the argument at the time $t_3$ and the argument at the time $t_4$, and the difference between the argument at the time $t_4$ and the argument at the time $t_5$ are all equal to $\omega$. Then, we can obtain the following equation:

$$\theta_d = \omega \cdot 3 \qquad (9)$$

From the equations (7) and (9), we can obtain the following equations:

$$3\omega = (\theta_5 - \theta_2) + 2\pi n \qquad (10)$$

$$n = \{3\omega - (\theta_5 - \theta_2)\}/2\pi \qquad (11)$$

Since n is an integer, the equation (11) can be rewritten as follows:

$$n = \text{ROUND}\{[3\omega - (\theta_5 - \theta_2)]/2\pi\} \qquad (12)$$

where ROUND(x) indicates that the value x is rounded to the nearest whole number.

When the value of n thus obtained is used in equation (7), we can obtain the true difference $\theta_d$ in argument between the Doppler data $Z_2$ and the Doppler data $Z_5$. By using this difference $\theta_d$, the argument $\theta_3$ and the argument $\theta_4$ are given by the following equations:

$$\theta_3 = \theta_2 + \theta_d/3 \qquad (13)$$

$$\theta_4 = \theta_2 + 2\theta_d/3 \qquad (14)$$

In addition to the above method, the Doppler data $\hat{Z}_3$ and $\hat{Z}_4$ may be calculated in such a manner that the absolute value of the Doppler data which has been last measured is used as the absolute values of the Doppler data $\hat{Z}_3$ and $\hat{Z}_4$.

Figure 8:
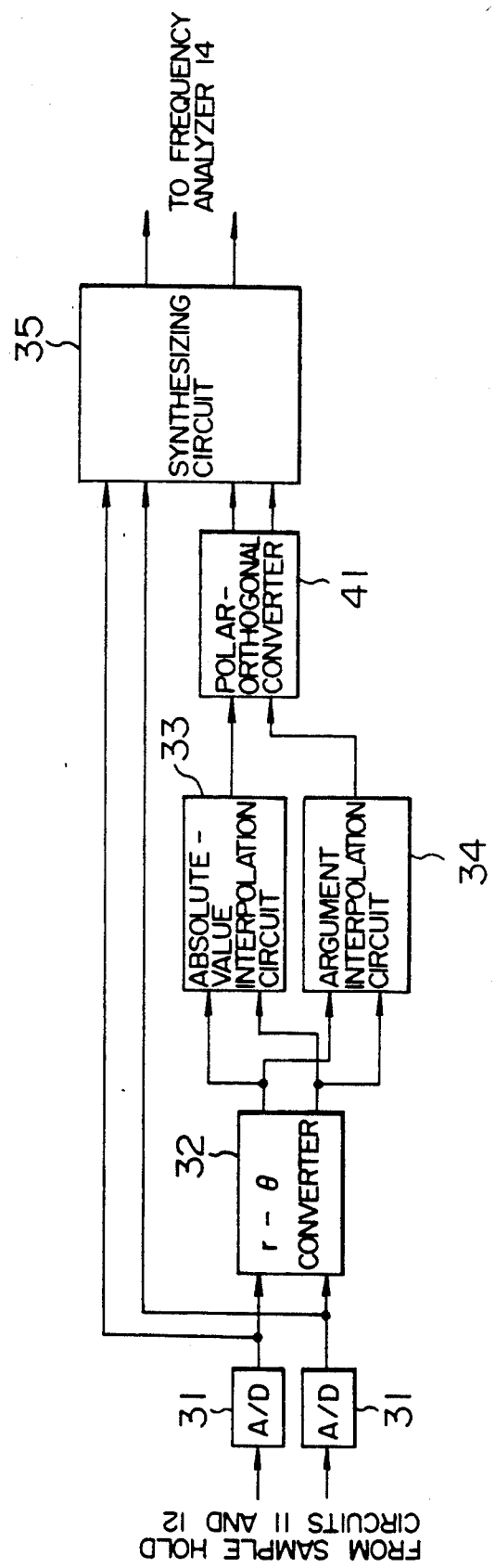
FIG. 8 is a block diagram showing a third example of the interpolation circuit of FIG. 3.

FIG. 8 shows a further example of the interpolation circuit 13. Referring to FIG. 8, an polar-orthogonal converter 41 is interposed between the synthesizing circuit 41 and each of the absolute-value interpolation circuit 33 and the argument interpolation circuit 34, to send out orthogonal coordinate values of supplementary Doppler data. Other circuit parts of the present example are identical with those of the example of FIG. 7.

Figure 9:
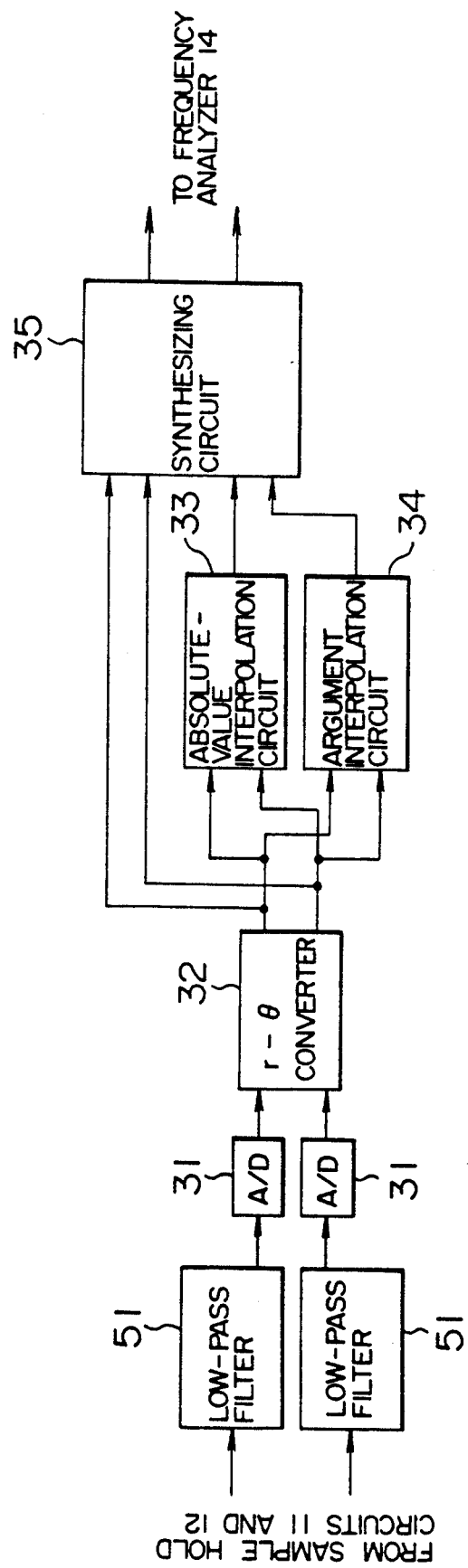
FIG. 9 is a block diagram showing a fourth example of the interpolation circuit of FIG. 3.

FIG. 9 shows still another example of the interpolation circuit 13. The example of FIG. 9 is different from the example of FIG. 7 only in that low-pass filters 51 are additionally provided, to remove a clutter component.

Figure 10:
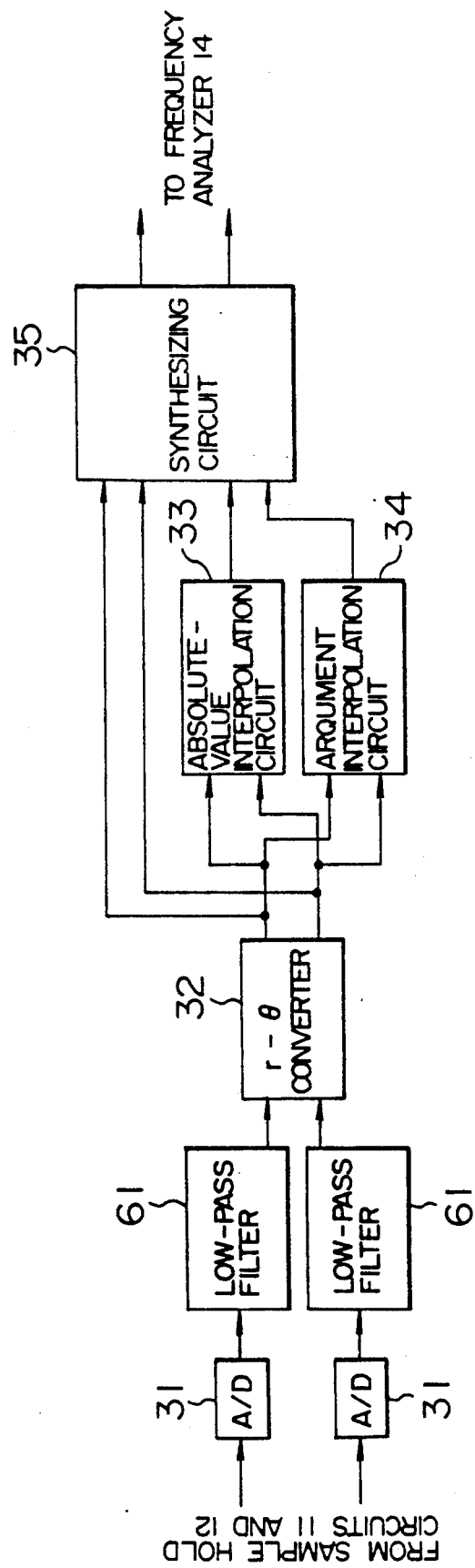
FIG. 10 is a block diagram showing a fifth example of the interpolation circuit of FIG. 3.

FIG. 10 shows still a further example of the interpolation circuit 13. In this example, digital filters 61 are used as low-pass filters for removing the clutter component.

As mentioned above, in the case where the Doppler scanning is carried out twice, the B-mode scanning is then carried out twice, and this combination of scanning is repeatedly carried out, missing Doppler data in the B-mode scanning period can be correctly calculated. Accordingly, a blood flow detection ability can be obtained which corresponds to the maximum moving speed of blood detected when the embodiment is operated only in the Doppler mode. Further, the Doppler scanning period is equal to the B-mode scanning period. Accordingly, the reduction in the frame rate of the tomogram based upon the B-mode scanning is not large, and thus the tomogram can be displayed in real time.

Next, a further example of the operation of the present embodiment will be explained, with reference to FIGS. 11A to 11F.

The transmitting/scanning circuit 2 sends out two Doppler pulses D and then sends out one B-mode pulse B in a period which is twice as long as the repetition period of the Doppler pulses, as shown in FIG. 11A. As shown in FIG. 11B, the switch 5 sends the output of the receiving/scanning circuit 3 to the mixers 7 and 8 in each of periods $P_1$ and $P_3$ (namely, the Doppler scanning periods), and sends the output of the receiving/scanning circuit 3 to the detection circuit 6 in the period $P_2$ (namely, the B-mode scanning period). In the B-mode scanning period $P_2$, information on a single scanning line for forming a tomogram due to the B-mode is detected, and the detection circuit 6 carries out envelope detection for the information. In this case, the information on the scanning line can include information from a portion two times greater in depth than a portion which can be measured by the operation shown in FIGS. 6A and 6B. In the Doppler scanning periods $P_1$ and $P_3$, as shown in FIG. 11E, the sample/hold circuits 11 and 12 perform sampling operations for the quadrature phase detection output from the mixers 7 and 8 at times $t_1$, $t_2$, $t_5$ and $t_6$ in accordance with the Doppler gate signal of FIG. 11D. In the interpolation circuit 13, as shown in FIG. 11F, Doppler signals $\hat{Z}_3$ and $\hat{Z}_4$, which would be obtained at times $t_3$ and $t_4$ if the B-mode scanning period $P_2$ were a Doppler scanning period, are calculated on the basis of Doppler data at the time moments $t_1$, $t_2$, $t_5$ and $t_6$. According to the above-mentioned B/D mode, a blood flow detection ability can be obtained which corresponds to the maximum blood speed detected when the embodiment is operated only in the Doppler mode, and moreover a tomogram due to the B-mode can include a portion two times greater in depth than a portion which can be measured by the operation shown in FIGS. 6A and 6B. Further, the time between the B-mode pulse and the subsequent Doppler pulse is twice as long as the repetition period the Doppler pulses. Accordingly, the influence of a residual echo due to the B-mode pulse on the Doppler signal is reduced, and thus the S/N ratio of the Doppler signal is improved.

Further, according to still another example of the operation of the present embodiment as shown in FIGS. 12A to 12F, Doppler data $Z_4$, which is obtained immediately after the B-mode scanning period $P_2$, is not used for calculating missing Doppler data $\hat{Z}_3$, and moreover the Doppler data $Z_4$ is replaced by a Doppler signal $\hat{Z}_4$ which is calculated from Doppler data $Z_1$, $Z_2$, $Z_5$ and $Z_6$. Thus, the adverse effect of the transient response of the present embodiment on the results of measurement is reduced.

As is evident from the above explanation, according to the present invention, supplementary data is calculated on the basis of the difference in argument between adjacent complex Doppler shift data. Thus, in the B/D mode where a B-mode operation and a Doppler mode operation are alternately performed, missing Doppler data in the period when the Doppler mode operation is stopped can be correctly calculated.

Further, according to the present invention, even if the Doppler shift data has a frequency corresponding to half of the repetition frequency of the transmitted pulses in the Doppler mode, supplementary data can be correctly calculated.

Furthermore, when an ultrasonic Doppler blood flowmeter is operated in the B/D mode, missing Doppler data in the B-mode scanning period can be correctly calculated on the basis of the absolute value and argument of measured, complex Doppler data. Accordingly, in the B/D mode, the blood flowmeter has a blood flow detection ability corresponding to the maximum blood speed detected when the blood flowmeter is operated only in the Doppler mode.

Additionally, according to the present invention, even if the Doppler mode operation is stopped for a period that is two or more times as long as the Doppler sampling period, missing Doppler data in the period when the Doppler mode operation was stopped can be correctly calculated. That is, the Doppler mode operation can be stopped for a relatively long period, and thus an ultrasonic Doppler shift blood flowmeter can be operated in the B/D mode without arousing serious problems.

We claim:

1. An ultrasonic Doppler blood flowmeter for inspecting a body which includes a movable scatterer to obtain information relating to the speed of the scatterer, said flowmeter comprising:

ultrasonic transmitting/receiving means for transmitting ultrasonic pulses into the body during a Doppler scanning period having a plurality of cycles of equal duration and for receiving ultrasonic pulses reflected from inside the body, an ultrasonic pulse being transmitted during a predetermined portion of each cycle and a reflected signal being received during each cycle, the ultrasonic transmitting-/receiving means including means for generating an ultrasonic echo signal from each reflected pulse;

an oscillator which generates an oscillator signal;

complex Doppler shift signal generating means operative, when activated, for generating a complex Doppler shift signal during each cycle on the basis of the ultrasonic echo signal and the oscillator signal, each complex Doppler shift signal having a respective argument;

control means for selectively activating and deactivating the complex Doppler shift signal generating means;

calculating means for calculating a supplementary Doppler shift signal, after the Doppler scanning period and while the Doppler shift signal generating means is deactivated, on the basis of a difference in argument between the complex Doppler shift signals generating during two consecutive cycles; and frequency analyzer means for determining the information relating to the speed of the scatterer from the complex Doppler shift signals and the supplementary Doppler shift signal.

2. An ultrasonic Doppler blood flowmeter according to claim 1, wherein the calculating means comprises means for calculating the supplementary Doppler shift signal by extrapolation based on the difference in argument.

3. An ultrasonic blood flowmeter for inspecting a body having a movable scatterer to obtain information relating to the speed of the scatterer, comprising:

ultrasonic transmitting/receiving means for transmitting ultrasonic pulses into the body during a sequence of Doppler scanning periods and further scanning periods which separate the Doppler scanning periods, each Doppler scanning period having a plurality of cycles of equal duration, a pulse being transmitted during a predetermined portion of each cycle of every Doppler scanning period and at least one pulse being transmitted during each further scanning period, the ultrasonic transmitting/receiving means additionally including means for receiving ultrasonic pulses reflected from inside the body and for generating an ultrasonic echo signal from each reflected pulse;

an oscillator which generates an oscillator signal;

complex Doppler shift signal generating means operative, when activated, for generating a complex Doppler shift signal during each cycle of the Doppler scanning periods on the basis of the ultrasonic echo signals and the oscillator signal, each complex Doppler shift signal having a respective argument and a respective absolute value;

control means for activating the complex Doppler shift signal generating means during the Doppler scanning periods and for deactivating the complex Doppler shift signal generating means during the further scanning periods;

means for calculating at least one supplementary Doppler shift signal for each further scanning period, the means for calculating including argument calculating means for calculating an argument for each at least one supplementary Doppler shift signal on the basis of complex Doppler shift signals generated before and after the respective further scanning period and absolute value calculating means for calculating an absolute value for each at least one supplementary Doppler shift signal on the basis of complex Doppler shift signals generated before and after the respective further scanning period; and frequency analyzer means for calculating the information relating to the speed of the scatterer in the body from the Doppler shift signals and the supplementary Doppler shift signals.

4. An ultrasonic blood flowmeter according to claim 3, wherein each further scanning period has a duration which is at least as great as the duration of two cycles of a Doppler scanning period.

* * * * *